United States Patent [19]

Moriya

[11] Patent Number: 5,424,536

[45] Date of Patent: Jun. 13, 1995

[54] SUBSTRATE INTERNAL DEFECT AND EXTERNAL PARTICLE DETECTING APPARATUS USING S-POLARIZED AND P-POLARIZED LIGHT

[75] Inventor: Kazuo Moriya, Ageo, Japan

[73] Assignee: Mitsui Mining & Smelting Co., Ltd., Tokyo, Japan

[21] Appl. No.: 216,190

[22] Filed: Mar. 22, 1994

[30] Foreign Application Priority Data

Mar. 26, 1993 [JP] Japan ................................. 5-090594

[51] Int. Cl.6 ............................................. G02F 1/01
[52] U.S. Cl. ..................................... 250/225; 356/369
[58] Field of Search ................. 250/572, 225; 356/237, 356/364, 369, 337, 338, 341

[56] References Cited

U.S. PATENT DOCUMENTS 4,614,427  9/1986  Koizumi et al. .................... 356/237
4,893,932  1/1990  Knollenberg ........................ 356/369
5,046,847  9/1991  Nakata et al. ...................... 356/338
5,177,559  1/1973  Batchelder et al. ................. 356/237

Primary Examiner—David C. Nelms
Assistant Examiner—Steven L. Nichols
Attorney, Agent, or Firm—Bucknam and Archer

[57] ABSTRACT

A defect estimating apparatus includes a laser radiating unit For obliquely radiating laser light on a surface to be observed of an object to be inspected, an observing unit for observing, through the surface to be observed, scattered light produced From internal defects or particles of the object by refracted light of the laser light, and observing scattered light or reflected light produced from flaws or particles on the surface by tile laser light, and a component separating unit for allowing the observing unit to perform observation by using both light containing primarily a p-polarized light component of the laser light and light containing primarily an s-polarized light component of the laser light.

9 Claims, 6 Drawing Sheets

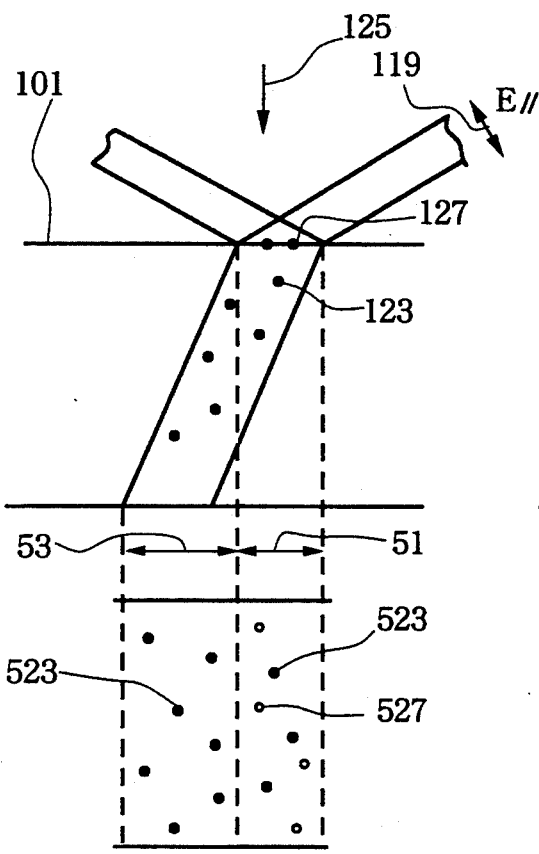 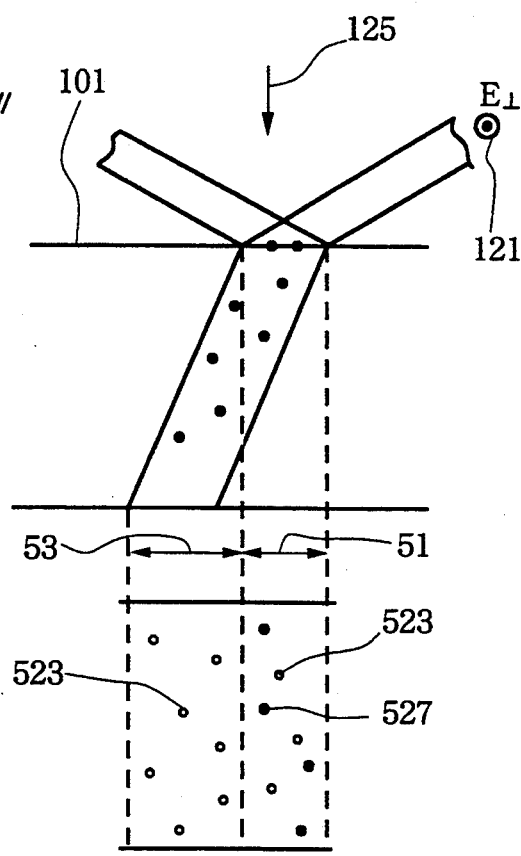
FIG. 5a                    FIG. 5b
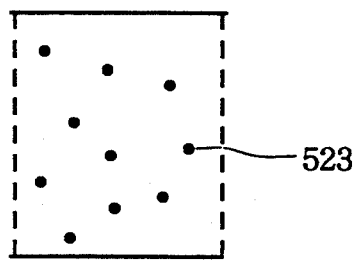 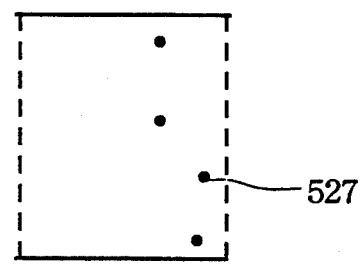
FIG. 6a                    FIG. 6b

SUBSTRATE INTERNAL DEFECT AND EXTERNAL PARTICLE DETECTING APPARATUS USING S-POLARIZED AND P-POLARIZED LIGHT

BACKGROUND OF THE INVENTION

1. Field of tile Invention

The present invention relates to an apparatus for estimating defects or particles of an object to be inspected such as a semiconductor wafer and, more particularly, to a defect estimating apparatus capable of performing observation of internal defects or particles of an object to be inspected by distinguishing them from particles or flaws on the surface of the object.

2. Prior Art

As an apparatus for estimating defects or the like of an object to be inspected such as a semiconductor wafer, there is a conventionally known apparatus in which laser light is obliquely incident on the surface of an object to be inspected, and the resulting scattered light from internal defects is observed through the surface of the object in a direction different from the incident direction of the laser light, thereby detecting internal defects or particles of the object (Japanese Patent Laid-Open No. 4-24541). In this apparatus, the influence of reflected light is minimized by observing the scattered light from an object to be inspected in the direction different from the incident direction of the laser light. In addition, by changing the wavelength of the laser light or the temperature of an object to be inspected, the depth to which the laser light enters the object can be adjusted.

In this conventional technique, however, in observing internal defects near the surface of an object to be inspected, flaws or the like present on the surface are also observed in the same field of observation. In addition, internal defects of an object to be inspected cannot be distinguished from flaws or the like on the surface of the object. This makes an accurate estimate Impossible.

SUMMARY OF THE INVENTION

The present invention has been made in consideration of the above situations and has as its object to provide a defect estimating apparatus capable of accurately estimating internal defects of an object to be inspected by clearly distinguishing the internal defects from flaws or the like present on the surface of the object.

To achieve the above object, the present invention provides a defect estimating apparatus which includes laser radiating means for obliquely radiating laser light on a plane surface of an object to be inspected, and observing means for observing, from the outside of the plane surface, scattered light produced from internal defects or particles of the object by refracted light of the laser light, and scattered light or reflected light produced from flaws or particles on the plane surface by the laser light, comprising component separating means for allowing the observing means to perform observation by using both light containing primarily a p-polarized light component of the laser light and light containing primarily an s-polarized light component of the laser light.

In the preferred embodiments of the present invention, the component separating means is a polarizer arranged between the laser radiating means and an object to be inspected. If the laser light to be radiated is randomly polarized light or laser light containing a p-polarized light component and an s-polarized light component, a polarizer arranged inside the observing means can be used as the component separating means. If the laser light to be radiated is linearly polarized light, a polarization rotator arranged between the laser radiating means and an object to be inspected can be used as the component separating means. If the laser light to be radiated is laser light containing a p-polarized light component and an s-polarized light component at a predetermined ratio or containing only p-polarized light component or s-polarized light component, a polarizing prism arranged inside the observing means can be used as the component separating means. In addition, the observing means includes image acquiring means for acquiring image data based on the scattered light or the reflected light through photoelectric conversion, and means for distinguishing images of internal defects or particles from images of flaws or defects on the plane surface on the basis of image data of at least two images, which are acquired by the image acquiring means by using primarily a p-polarized light component and an s-polarized light component obtained by the component separating means, and which include the same observation region.

BRIEF DESCRIPTION OF THE DRAWINGS

FIGS. 5a and 5b are schematic views each showing a section observed and an image obtained by the observation in the apparatus shown in FIG. 1;

FIGS. 6a and 6b are schematic views showing images obtained by extracting only images of internal defects or particles from the images shown in FIGS. 5A and 5B, respectively;

DESCRIPTION OF THE PREFERRED EMBODIMENTS

The preferred embodiments of the present invention will be described in derail below.

Figure 1:
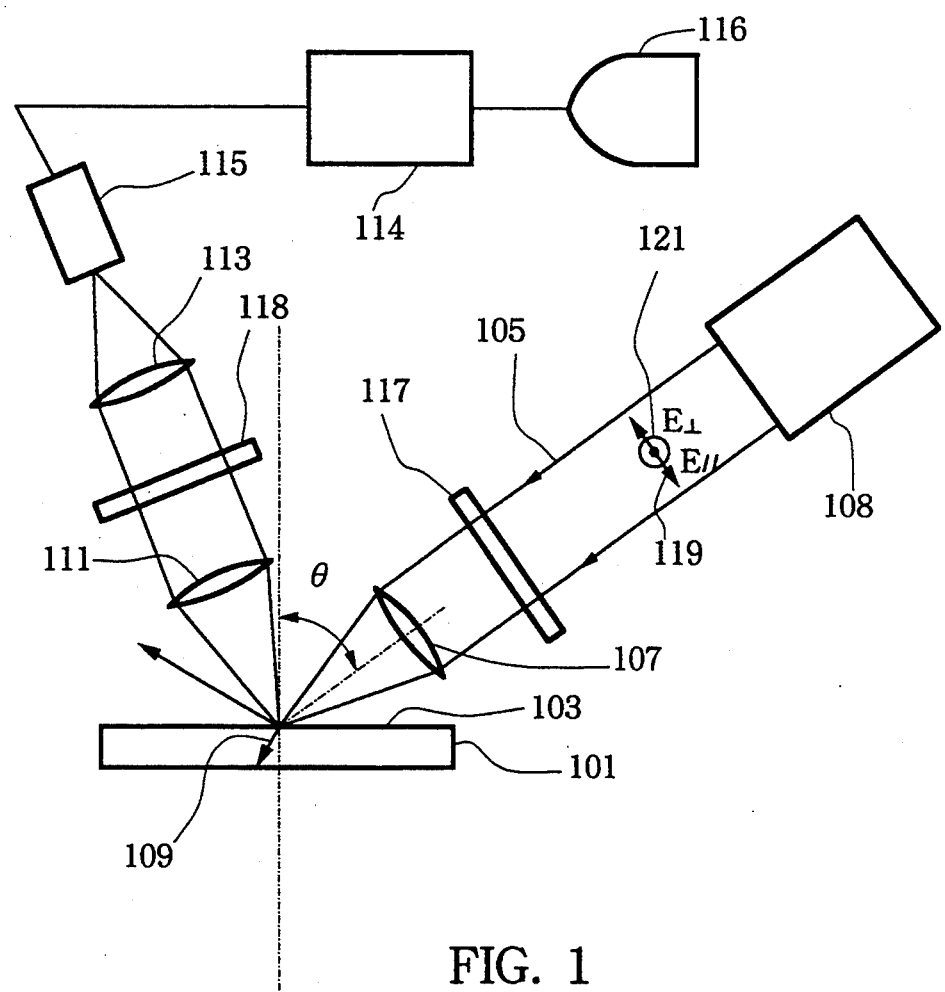
FIG. 1 is a schematic view showing the arrangement of a defect estimating apparatus according to one embodiment of the present invention.

FIG. 1 is a schematic view showing the according to one embodiment of the present invention. As shown in FIG. 1, this apparatus includes a laser device 108 for obliquely radiating laser light 105, through a condenser lens 107 onto a plane surface 103 of an object 101 to be inspected, and observing means for observing, from the outside of the plane surface 103, scattered light produced from internal defects or particles of the object by refracted light 109 of the laser light 105, and scattered light or reflected light produced from flaws or particles on the plane surface by the laser light. This observing means includes an observation lens 111, an image formation lens 113, and an image pickup device 115. The image pickup device 115 photoelectrically converts a scattered image or the like formed by the image formation lens 113 into image data. The observing means further includes an image processing device 114 for performing image processing, such as binarization, for the output image data from the image pickup device 115, and a CRT 116 for displaying the image data from the image pickup device 115 intact or displaying the processed result from the image processing device 114. Although not shown, the apparatus also includes a device for moving the object 101 to be inspected and, e.g., a CPU for controlling the overall apparatus.

This defect estimating apparatus with the above arrangement is similar to that disclosed in Japanese Patent Laid-Open No. 4-24541. However, the apparatus of this embodiment further includes a polarizing plate 117 for polarizing the laser light 105 before the condenser lens 107 so as to radiate light which consists primarily of a p-polarized light component 119 or an s-polarized light component 121, or in which the two components are mixed at a predetermined ratio. In addition, the image processing device 114 has a function of distinguishing images of internal defects or particles from images of flaws or defects on the surface 103 on the basis of image data of at least two images, which are obtained by using the p-polarized light component and the s-polarized light component, and which Include the same observation region, and a function of outputting the distinguished images independently of each other.

Figure 2:
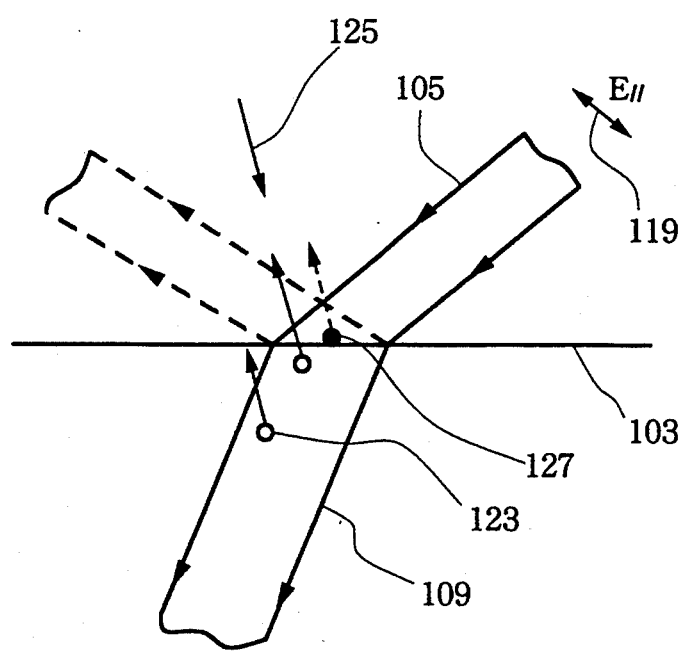
FIG. 2 is an enlarged view for explaining a method of performing observation by using primarily a p-polarized light component in the apparatus shown in FIG. 1.

Assume that observation is to be performed by this arrangement by using the p-polarized light component. In this case, the laser light 105 containing various polarized light components is radiated from the laser device 108 and polarized through the polarizing plate 117 whose rotating angle about the optical axis is so adjusted that the laser light 105 contains primarily the p-polarized light component 119. After being condensed through the condenser lens 107, the polarized laser light 105 is radiated on tile surface 103. As illustrated in an enlarged view of FIG. 2, the laser light 105 thus radiated contains primarily the p-polarized light component 119 and a large part of the p-polarized light component 119 is transmitted through the surface 103 to become the refracted light 109. Especially when an incident angle of the laser light 105 with respect to the surface 103 is the Brewster angle, the whole p-polarized light component is transmitted through the surface 103 to become the refracted light 109. When the refracted light 109 collides against internal defects or particles 123 of the object 101, scattered light is produced from the portions of collision. This scattered light is observed in a direction indicated by an arrow 125 through the surface 103. In this case, the scattered light of the s-polarized light component reflected by the surface 103 is weak compared with the scattered p-polarized light component. Consequently, the internal defects or particles 123 are observed more clearly than a flaw 127 or tile like on the surface 103.

Figure 3:
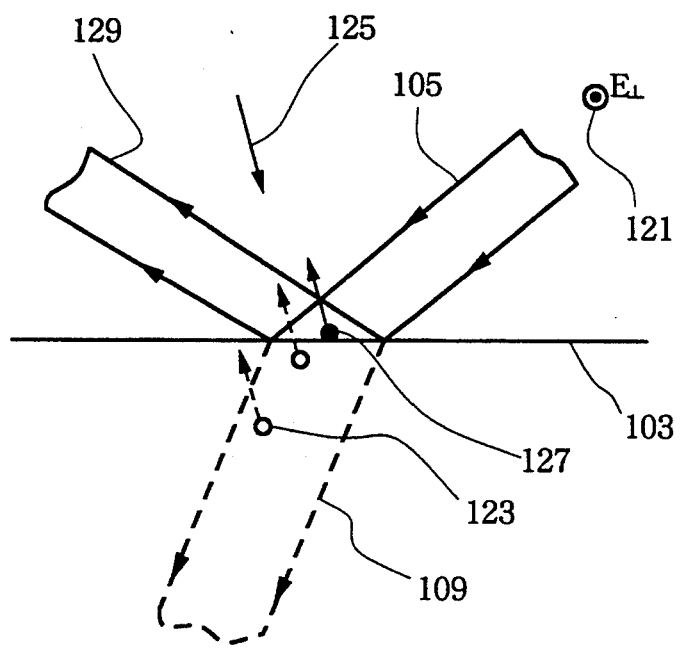
FIG. 3 is an enlarged view for explaining a method of performing observation by using primarily an s-polarized light component in tile apparatus shown in FIG. 1.

When observation is to be performed by using the s-polarized light component, as shown in an enlarged view of FIG. 3, the laser light 105 radiated from the laser device 108 is so polarized as to contain primarily the s-polarized light component 121 by adjusting the rotating angle of the polarizing plate 117. A large part of the s-polarized light component 121 is reflected by the surface 103 to be observed, producing reflected light 129. When the reflectance of the surface 103 is high as in this case, an electric field of light on the surface 103 is also high. Therefore, the scattered light produced from the flaw 127 or the like on the surface 103 is stronger than the scattered light from the internal defects or particles 123. Consequently, the flaw 127 or the like on tile surface 103 is observed more conspicuously than the internal defects or particles 123. This principle will be described below with reference to FIG. 4.

Figure 4:
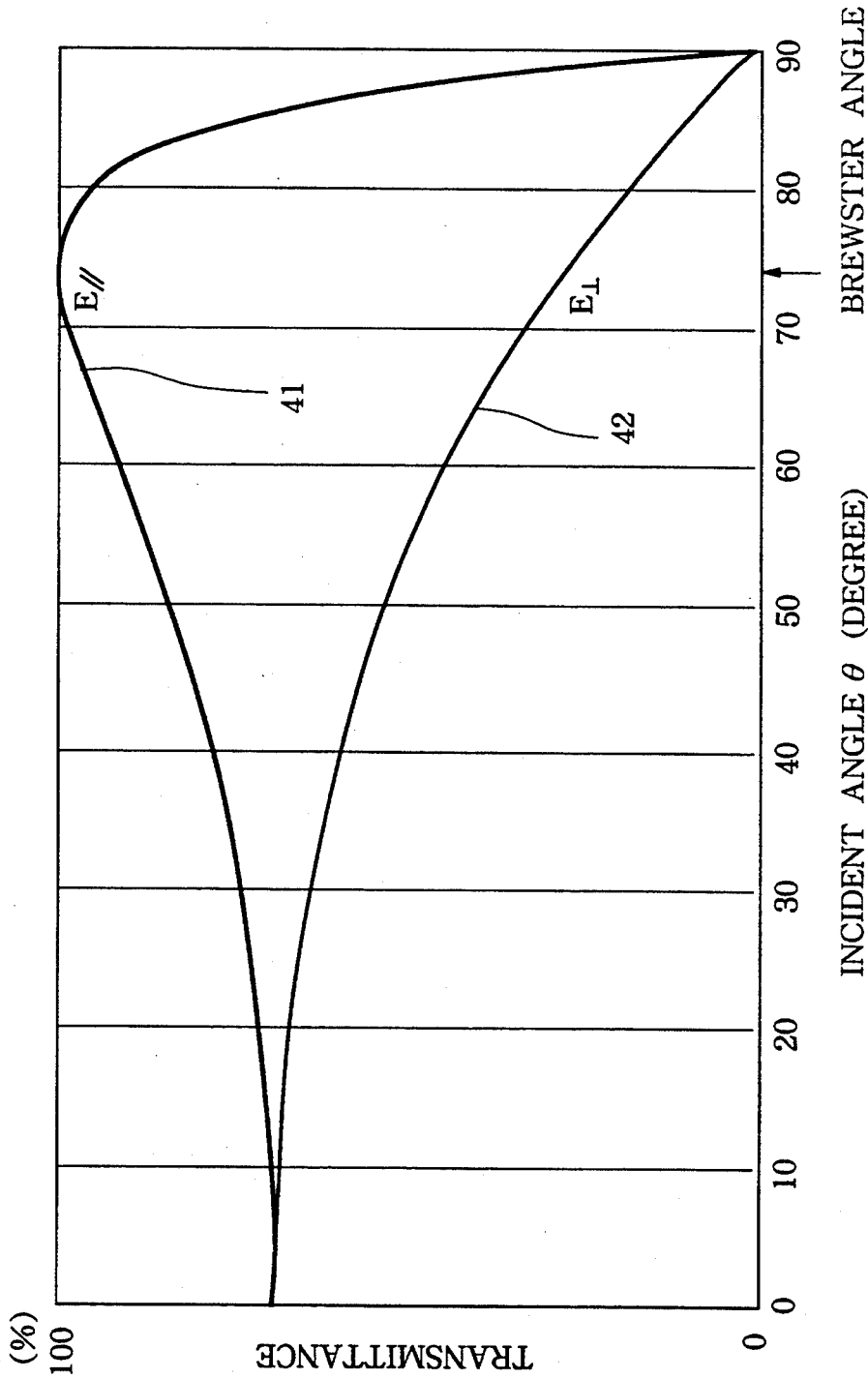
FIG. 4 is a graph showing a change in transmittance as a function of an incident angle for each of a p-polarized light component 41 and an s-polarized light component 42.

FIG. 4 is a graph showing curves 41 and 42 indicating changes In the transmittance as a function of the incident angle $\theta$ for the p-polarized light component and the s-polarized light component, respectively. As shown in FIG. 4, the ratio of the p-polarized light component which is not reflected by the surface 103 but is transmitted through it to become refracted light is very high. In particular, the transmittance is 100% at the Brewster angle. In contrast, as indicated by the curve 42, the ratio of the s-polarized light component which is reflected by the surface 103 is relatively high. Therefore, when observation is performed by using light containing primarily the p-polarized light component, the ratio of the light transmitted through the surface 103 to become refracted light is higher than that when observation is performed by using light containing primarily the s-polarized light component. Consequently, internal defects or the like are observed more clearly than flaws or the like on the surface 103 mainly by the scattered light from inside the object 101 to be inspected. When, in contrast, observation Is performed by using light containing primarily the s-polarized light component, the ratio of the reflected light is relatively high. Consequently, flaws or the like on the surface 103 are observed more conspicuously primarily by the scattered light from the surface 103. Therefore, in estimating internal defects close to the surface 103, even if the internal defects and flaws on the surface 103 are observed in the same observation field, it is possible to distinguish between the internal defects and the flaws on the surface 103 by comparing the observation field when observation is performed by using light containing primarily the p-polarized light component with that when observation is performed by using light containing primarily the s-polarized light component.

FIGS. 5a and 5b are schematic views showing images observed by the method as described above. When observation is performed by using the p-polarized light component, as shown in FIG. 5a, both images 523 of internal defects or particles and images 527 of flaws or the like on the surface 103 are observed in a region 51 in which the surface 103 and the interior of the object 101 to be inspected are observed in the same field of view in an observation direction 125. In this case, however, while the images 527 of the flaws or the like have a low light intensity, the images 523 of the defects or particles are observed with a high intensity. On the other hand, in a region 53 in which only the interior of the object to be inspected is observed, only the images 523 of the defects or particles are observed with a high intensity. When observation is performed by using the s-polarized light component, as shown in FIG. 5b, both the images 523 of the defects or particles and the images 527 of the flaws or the like are observed in the region 51. In this case, the images 527 of the flaws are observed with a high intensity, and the images 523 of the defects or particles are observed with a low intensity. In the region 53, only time images 523 of the defects or particles are observed with a low intensity.

FIG. 6a illustrates an image formed by extracting only the images 523 of the internal defects or particles from the image shown in FIG. 5a.

FIG. 6b illustrates an image formed by extracting only the images 527 of the flaws or the like from the image shown in FIG. 5b. The extraction of this sort can be performed by using the image processing device 114 in accordance with a conventional image processing method. For example, a threshold value k by which the intensity of the images 523 of the internal defects or particles can be distinguished from the intensity of the images 527 of the flaws or the like is set for intensities $I_a$ of the pixels of the image shown in FIG. 5a and intensities $I_b$ of the pixels of the image shown in FIG. 5b. Subsequently, tile image data of each pixel with the intensity $I_a$ satisfying tile relation $I_a > kI_b$ with respect to the intensity $I_b$ of the corresponding image data is left intact, and the image data of each pixel with the intensity $I_a$ satisfying the relation $I_a < kI_b$ is set at 0. Consequently, tile internal defects can be extracted. The surface defects can be extracted by performing the reverse manipulation.

Note that if the incident laser light is linearly polarized light. A polarization rotator can be used instead of the polarizing plate 117. Note also that if the incident light is either randomly polarized light or laser light containing both p- and s-polarized light components, a polarizer 118 can be inserted between the observation lens 111 and the image formation lens 113.

Figure 7:
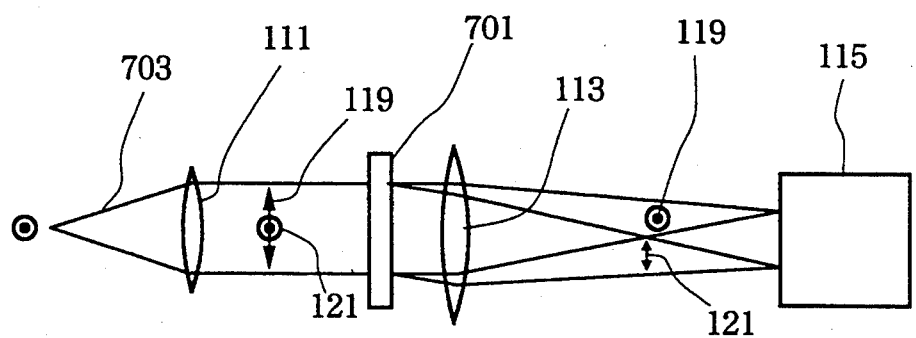
FIG. 7 is a schematic view showing the arrangement of observing means of a defect estimating apparatus according to another embodiment of the present invention.
Figure 8:
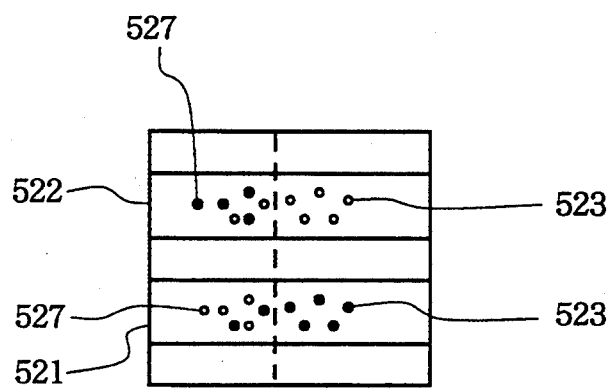
FIG. 8 is a schematic view showing an image observed by the apparatus shown in FIG. 7.

FIG. 7 is a schematic view showing the arrangement of observing means of a defect estimating apparatus according to another embodiment of the present invention. In this apparatus, as means for separating a p-polarized light component and an s-polarized light component from each other, a polarizing prism 701 such as a Wollaston prism is arranged between an observation lens (objective lens) 111 and an image formation lens 113, instead of the polarizing plate 118 of the above embodiment. In this arrangement, laser light to be incident on an object to be inspected contains an s-polarized light component and a p-polarized light component at a predetermined ratio. Therefore, the scattered light produced from internal defects or flaws on the plane surface by this laser light also contains a p-polarized light component 119 and an s-polarized light component 121. This scattered light is separated through the polarizing prism 701, thereby forming, as shown in FIG. 8, an image 521 resulting from the p-polarized light component and an image 522 resulting from the s-polarized light component at the same time on an image pickup device 115. Note that images 523 formed by the scattered light from the internal defects or particles are observed with a high intensity in the region of the image 521, and images 527 formed by tile scattered light from the flaws or the like on the surface are observed with a high intensity in the region of the image 522.

This apparatus has an advantage that measurements can be performed accurately since the beam position of the laser light does not change due to rotation of a polarizing plate or the like. The apparatus also has an advantage that the measurement time is short because it is unnecessary to, e.g., adjust the rotating position of a polarizing plate or the like.

Figure 9:
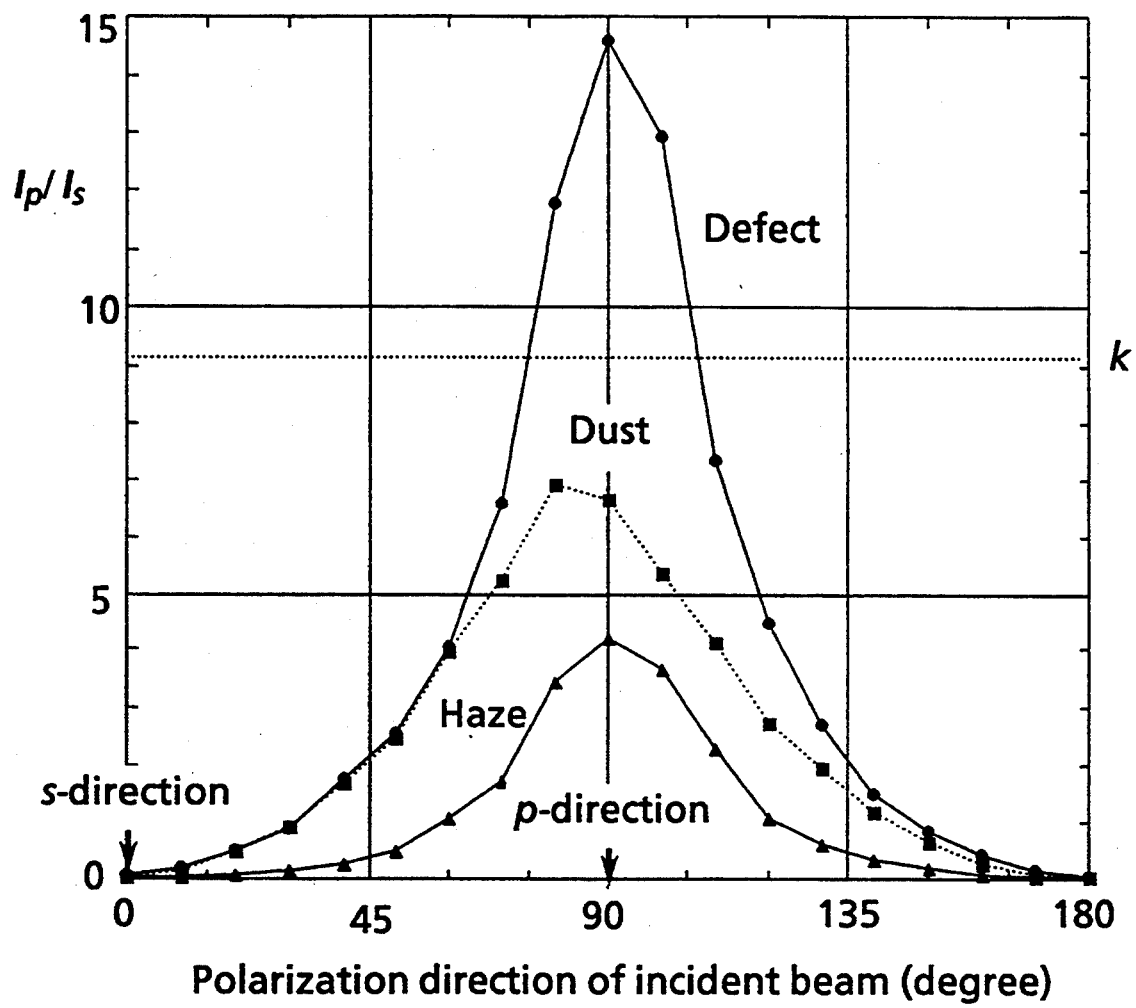
FIG. 9 is a graph showing a change in the ratio of intensity of image data formed by the p-polarized component to that formed by the s-polarized component as a function of polarization direction of an incident light.

Moreover, even when the laser light to be incident on the object 101 contains only p-polarized light component, there is the case where the scattered light from the internal defects or flaws on the plane surface contains all s-polarized component as well as the p-polarized component due to depolarization as indicated in FIG. 9 Also in this case, the scattered light is separated by the polarization prism 701, and forms images 521 and 522 respectively of the p-polarized component; and the s-polarized component at the same time on the image pick up device 115 as indicated in FIG. 8. In this case, both of the scattered light from the flaws or particles (haze or dust) on the plane and surface and the scattered light from the internal defects contain p-polarized light component and s-polarized light component. However, the ratio of intensity of the p-polarized component to the s-polarized component in case of the scattered light from the internal defects is larger than that in case of the scattered light from the plane surface. Therefore, the ratio of the intensity $I_p$ of each pixel data of the image 521 to the intensity $I_s$ of corresponding data of the image 522 in case of the internal defects can be distinguished by an appropriate threshold value k from that in case of the haze (micro roughness) or dust as illustrated in FIG. 9. By the use of this principle, the image processing device 114 can obtain images of the internal defects and images of the surface plane separately as explained above with reference to FIGS. 5a, 5b, 6a, and 6b. That is, with respect to a pair of the intensities $I_p$ and $I_s$, if $I_p > kI_s$, the intensities are of the data of an internal defer, and if $I_p < kI_s$, the intensities are of the data of a haze or dust.

According to the present invention as has been described above. Observation can be performed by using both light containing primarily a p-polarized light component and light containing primarily an s-polarized light component. This makes it possible to separately estimate internal defects or particles and flaws or the like on the surface. In addition, by arranging the polarizing prism inside the observing means, internal defects or particles and flaws or the like on the surface can be simultaneously observed, resulting a short estimation time.

What is claimed is:

1. A defect estimating apparatus which includes laser radiating means for obliquely radiating laser light on a plane surface of an object to be inspected, said object having a plane surface and an interior, and observing means for observing, from the outside of said plane surface, images formed by scattered light produced from defects or particles in the interior of the object by refracted light of the laser light, and images formed by scattered light or reflected light produced from flaws or particles on said plane surface by the laser light, comprising:

component separating means for allowing said observing means to perform observation by using both light containing primarily a p-polarized light component of said laser light and light containing primarily an s-polarized light component of said laser light, and distinction means for distinguishing, in said observed images, the images of defects or particles in the interior of said object from the images of flaws or particles on said plane surface on the basis of the intensities of said both lights each. Forming the images of the same defects or particles in said interior and flaws or particles on said plane surface.

2. The apparatus according to claim 1 wherein said component separating means is a polarizer disposed between said laser radiating means and said object to be inspected.

3. An apparatus according to claim 1, wherein the laser light to be radiated is randomly polarized light or laser light containing a p-polarized light component and an s-polarized light component, and said component separating means is a polarizer disposed inside said observing means.

4. The apparatus according to claim 1 wherein the laser light to be radiated is linearly polarized light, and said component separating means is a polarization rotator disposed between said laser radiating means and said object to be inspected.

5. The apparatus according to claim 1 which comprises an image pick-up device and wherein the laser light to be radiated is laser light containing a p-polarized light component and an s-polarized light component at a predetermined ratio, said component separating means is a polarizing prism disposed inside said observing means, and said observing means forms an image resulting from the p-polarized light component and an image resulting from the s-polarized light component at the same time on said image pickup device.

6. The apparatus according to claim 1 wherein the laser light to be radiated is a p-polarized light, and said component separating means is a polarizing prism disposed inside said observing means.

7. The apparatus according to claim 1, wherein said observing means includes image acquiring means for acquiring image data based on the scattered light or the reflected light through photoelectric conversion, and said distinction means distinguishes the images of defects or particles in the interior of said object from the images of flaws or defects on said plane surface on the basis of the intensities of the image data which are acquired by said image acquiring means by using primarily a p-polarized light component and an s-polarized light component obtained by said component separating means.

8. The apparatus according to claim 7, wherein each image has a pixel and said distinction means determine whether each pixel of the images acquired by using primarily a p-polarized light component is of the defects or particles in the interior of said object or of the flaws or particles on said plane surface by judging whether the intensity $I_a$ of the image data of the pixel satisfies the relation $I_a > kI_b$ or not with respect to the intensity $I_b$ of the corresponding image data acquired by using primarily an s-polarized light component, wherein k is a constant value.

9. A defect estimating apparatus which includes laser radiating means for obliquely radiating laser light on a plane surface of an object to be inspected, said object having an interior and a plane surface, observing means for observing from the outside of the plane surface images formed by scattered light produced from defects or particles in the interior of said object by refracted light of the laser light, and images formed by scattered light or reflected light produced from flaws or particles on said plane surface by the laser light, and component separating means for allowing said observing means to perform observation by using both light containing primarily a p-polarized light component of the laser light and light containing primarily an s-polarized light component of the laser light, wherein the apparatus comprises an image pick-up device and the laser light to be radiated is laser light containing a p-polarized light component and an s-polarized light component at a predetermined ratio, said component separating means is a polarizing prism arranged inside said observing means, and said observing means forms an image resulting from the p-polarized light component and an image resulting from the s-polarized light component at the same time on said image pickup device.

* * * * *